United States Patent [19]

Inada et al.

[11] Patent Number: 4,968,787

[45] Date of Patent: Nov. 6, 1990

[54] METHOD FOR TREATING GLYCOSIDE

[75] Inventors: Shoshichiro Inada, Amagasaki; Johji Ogasawara; Masakazu Takahashi, both of Kobe, all of Japan

[73] Assignee: Seitetsu Kagaku Co., Ltd., Japan

[21] Appl. No.: 78,189

[22] Filed: Jul. 27, 1987

[30] Foreign Application Priority Data

Jul. 28, 1986 [JP] Japan ................................ 61-178384

[51] Int. Cl.[5] .......................... C07H 1/06; C07H 1/08

[52] U.S. Cl. .................................... 536/18.5; 536/4.1; 536/124; 536/127

[58] Field of Search ........................ 536/4.1, 18.5, 124, 536/127, 1.1

[56] References Cited

U.S. PATENT DOCUMENTS

| | | | |
|---|---|---|---|
| 3,856,941 | 12/1974 | Satoh | 514/26 |
| 4,555,504 | 11/1985 | Jones | 514/26 |
| 4,663,316 | 5/1987 | Ninger et al. | 514/99 |
| 4,675,395 | 6/1987 | Fukazawa et al. | 536/103 |
| 4,749,522 | 6/1988 | Kamarei | 514/169 |
| 4,764,604 | 8/1988 | Muller | 536/103 |
| 4,778,787 | 10/1988 | Catsimpoolas et al. | 514/25 |
| 4,857,329 | 8/1989 | Sako et al. | 424/195.1 |

FOREIGN PATENT DOCUMENTS

| | | | |
|---|---|---|---|
| 0001688 | 2/1979 | European Pat. Off. . | |
| 2633490 | 2/1978 | Fed. Rep. of Germany | 514/27 |
| 62-0496 | 1/1987 | Japan | 536/18.5 |
| 1382576 | 2/1975 | United Kingdom | 536/18.1 |

OTHER PUBLICATIONS

Saunders et al.; Carbohydrdate Research, 5(4):453–460, (1967).

Mitsuo et al.; Chem. Pharm. Bull., 32(3):1183–1187, (1984).

Mostad; J. of Chromatography, 396:157–168, Jun. 19, 1987.

Stahl et al.; Chemical Abstracts, 102:79194x, (1985), pp. 630–631.

Jiyuntendou et al., *Patent Abstracts of Japan,* 5(16):832 (C 75), (1981).

Ghosal et al., *Chem. Abstracts,* 100(3):299, (No. 204142), (1984).

Su et al., *Chem. Abstracts,* 79(6):214, (No. 35069n), (1973).

*Primary Examiner*—Ronald W. Griffin
*Assistant Examiner*—Nancy S. Carson
*Attorney, Agent, or Firm*—Saidman, Sterne, Kessler & Goldstein

[57] ABSTRACT

A method for extracting and separating an aglycone which constitutes a glycoside, said method comprises steps of:

subjecting a material containing the glycoside to hydrolysis to decompose the glycoside into a sugar moiety and an aglycone;

extracting the aglycone from the hydrolyzed material by using a fluid at supercritical or subcritical conditions as an extraction agent; and separating the extracted aglycone from the extraction agent.

10 Claims, 1 Drawing Sheet

METHOD FOR TREATING GLYCOSIDE

FIELD OF THE INVENTION

The present invention relates to a method for treating a glycoside. More particularly, it relates to a method for extracting and separating a non-sugar moiety having physiological activities from a glycoside.

BACKGROUND OF THE INVENTION

Glycosides are one of components widely distributed in botanical world, and are decomposed into sugar moieties and non-sugar moieties with a suitable acid, alkali or hydrolytic enzyme.

Generally, a non-sugar moiety is called as an aglycone and, particularly, in the case that an aglycone is a steroid, it is called as a genin. Depending upon chemical structures of non-sugar moieties, glycosides are divided into alkyl glycosides, phenol glycosides, cyanate glycosides, mustard oil glycosides, coumarin or oxycoumarin glycosides, flavonoid glycosides, anthraquinone glycosides and the like. Further, glycosides are also classified according to their physical and chemical properties such as saponins, cardiotonic glycosides, bitter glycoside and the like.

Regarding the significance of the existence of a glycoside in a plant, there can not be found any established theory and it is said that a plant converts a noxious substance in its metabolites into a glycoside to render the substance innocuous, or a glycoside is a stored substance.

Usually, a non-sugar moiety is attached to a sugar moiety through ether bond but, in a mustard oil glycoside, it is attached to a sugar moiety through thioglycoside bond.

When a sugar moiety is glucose, such a glycoside is called as a glucoside. Although there can be two kinds of glucosides, namely $\alpha$- and $\beta$-glucosides, $\beta$- glucoside is predominant, which is hydrolyzed by $\beta$-glucosidase. Examples of a sugar moiety include hexoses such as glucose, fructose, mannose, galactose, etc.; and pentoses such as xylose, arabinose, etc. Further, according to the number of sugars, monosaccharides, disaccharides, trisaccharides and the like are included.

Examples of a non-sugar moiety called aglycone or genin includes alkaloids, steroids, saponins, flavonoids and the like and many of them have remarkable physiological activities against animals. Therefore, they are utilized as important substances in medicines, toxicants, perfumes, seasonings, pigments and the like.

Usually, these useful substances are extracted and separated with organic solvents, aqueous solvents and the like and then subjected to a treatment suitable for a particular purpose, for example, concentration, fractionation, purification and the like.

In this regard, a glycoside is extracted and separated from a plant or other suitable starting material in its intact form, or a free aglycone is extracted by hydrolyzing a glycoside in the starting material into a sugar moiety and a non-sugar moiety during treatment thereof. That is, usually, extraction and separation of a glycoside with an organic solvent or an aqueous solvent is carried out with paying attention to hydrolysis of the glycoside to obtain the glycoside in its intact form, or without paying any special attention to hydrolysis. For obtaining a glycoside in its intact form, it is of importance to inhibit the action of a hydrolytic enzyme present in a plant or other starting material and it is necessary to pay attention to secondary changes during operation. pH and temperature conditions are also of importance.

When extraction and separation are carried out without paying any special attention to hydrolysis, usually, an aglycone is liable to be affected by a certain factor except that the aglycone is stable against an extraction solvent, extraction conditions, coexisting substances and the like.

Recently, an attempt has been made to extract and separate a glycoside from a plant by using a fluid at supercritical conditions, particularly, carbon dioxide at supercritical conditions as an extraction agent. However, it is difficult to extract saccharides and glycosides having many polar groups with carbon dioxide alone under such pressure conditions as at 200 to 300 kg/cm$^2$ which is considered to be economical. In view of this, it has been reported to carry out extraction with addition of water, ethanol or the like as an extraction auxiliary (entrainer) to impart polarity to carbon dioxide extraction agent. However, it is still inefficient.

Since a sugar moiety of a glycoside is not specifically utilized as an objective substance having physiologically activities as described above and the objective substance to be extracted must be its aglycone, it is considered that a desired result can be achieved only by extracting and separating an aglycone without any impairment in its quality.

In a conventional method, extraction of an aglycone is carried out by allowing to stand a cut or pulverized starting material of a plant under humidified and warmed conditions for a long period of time to activate a hydrolytic enzyme contained in the material itself to hydrolyze a glycoside into a sugar moiety and a non-sugar moiety, or by subjecting a cut or pulverized starting material to hydrolysis in an organic solvent or an aqueous solvent for a long period of time with adjusting pH at an elevated temperature. In this case, an aglycone is liable to impair its quality because extraction takes a long period of time and it is affected by pH and temperature conditions, coexisting substances and the like. Further, when the aglycone is separated from an extraction solvent, there is such a defect that a light fraction is liable to scattered and lost.

OBJECTS OF THE PRESENT INVENTION

Under these circumstances, the present inventors have studied intensively to find out an industrially advantageous method for extracting and separating an aglycone of a glycoside in a plant or other starting material. As the result, it has been found that extraction and separation of an aglycone can be advantageously carried out without defects in a conventional method by positively subjecting a plant or other starting material to hydrolysis before or during extraction with a fluid at supercritical or subcritical conditions as an extraction agent.

Further, the present inventors have studied a variety of a starting material, a variety of an extraction agent, extraction and separation conditions and the like and attained to the present invention.

That is, the main object of the present invention is to provide an improved method for extracting and separating an aglycone from a plant or other starting material.

This object as well as other objects and advantages of the present invention will become apparent to those skilled in the art from the following description with reference to the accompanying drawings.

SUMMARY OF THE INVENTION

Figure 1:
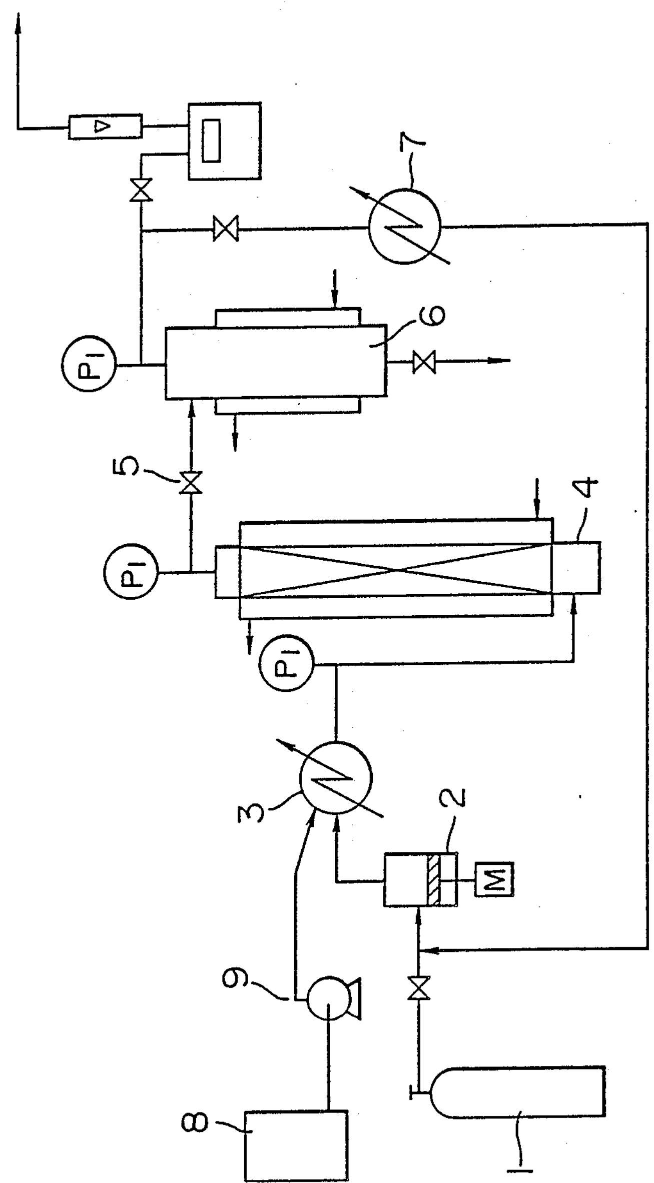
FIG. 1 is a flow sheet illustrating one embodiment of the method of the present invention.

According to the present invention, there is provided a method for extracting and separating an aglycone which constitutes a glycoside, said method comprises steps of:

subjecting a material containing the glycoside to hydrolysis to decompose the glycoside into a sugar moiety and an aglycone:

extracting the aglycone from the hydrolyzed material by using a fluid at supercritical or subcritical conditions as an extraction agent: and separating the extracted aglycone from the extraction agent.

DETAILED DESCRIPTION OF THE INVENTION

The method of the present invention can be applied to any type of glycosides contained in any plant and other starting materials.

The starting material to be used in the method of the present invention is not limited to a specific one and any starting material containing a glycoside can be used. For example, a starting material may be a plant itself or, preferably, a dried, cut or pulverized material in view of acceleration of hydrolysis of the glycoside. Or, a crude isolated glycoside can be used as the starting material.

In the method of the present invention, hydrolysis is positively effected before or at the same time of extraction. The hydrolysis is not limited, either and can be carried out a known method. For example, there can be employed a conventional acid or alkali hydrolysis. Or, hydrolysis can be carried out by humidifying and warming the starting material. An enzymatic hydrolysis can be also employed with addition of a suitable hydrolytic enzyme. When an enzyme is used, generally, hydrolysis is carried out at about 30 to 50° C. for several hours to several tens of hours depending upon a particular enzyme used. It is preferred to employ suitable hydrolysis conditions to positively accelerate hydrolysis to release a desired aglycone as quickly as possible.

The hydrolysis can be carried out in a separate container and then the hydrolyzed material can be introduced in an extractor. Alternatively, the hydrolysis can be carried out in an extractor before extraction or during extraction. A desired result may be obtained by the latter manner.

The fluid at subcritical or supercritical conditions used as the extraction agent in the present invention is that at about or beyond the critical temperature and the critical pressure. For example, it is a fluid at about or beyond the critical state having a density close to a liquid and a large diffusion coefficient close to a gas such as ethylene (9.9° C. 50 atm) and carbon dioxide (31.0° C., 72.9 atm). Examples of the fluid also include ammonia, $N_2O$, propane, water or the like. Because of these properties, the fluid can efficiently extract a large amount of various compounds quickly. Further, separation of the extraction agent from an extract can be readily effected. Furthermore, since dissolving power of the fluid for various compounds can be greatly varied only by a slight change in pressure or temperature, selective extraction can be effected. In the present invention, generally, any fluid at subcritical or supercritical conditions can be used. However, usually, it is preferred to use carbon dioxide as the extraction agent in view of its various advantages. For example, carbon dioxide is excellent in general extraction and separation abilities. Further, treatment can be carried out at a relatively low temperature with easy and simple handling and operation, which makes the method economical. Furthermore, carbon dioxide is inactive to almost all compounds under treatment conditions.

By the way, depending upon a starting material to be treated, carbon dioxide may act as carbonic acid in the presence of water, it is necessary to previously examine extraction agents to choose an extraction agent suitable for a particular starting material. Particularly, when hydrolysis and extraction are carried out simultaneously, it is necessary to pay attention to the effect of carbonic acid derived from carbon dioxide in the presence of water. In addition, it is necessary to pay attention to the effect of carbon dioxide on a hydrolytic enzyme and to choose an enzyme which is hardly inactivated by the extraction agent.

Extraction can be carried out at subcritical or supercritical conditions of the extraction agent and separation of the extracted aglycone from the extraction agent can be readily effected by reducing pressure, for example, to atmospheric pressure.

The method of the present invention can be carried out in a batchwise operation or continuously.

In the case that the separated aglycone is unstable as such, or it is necessary to support it on a certain carrier for a special use, it is possible to absorb the aglycone on a porous absorbent such as active carbon, or to include the aglycone in a host compound such as cyclodextrin to form an inclusion complex to obtain the aglycone in a stable form.

The aglycone thus separated can be utilized as important substances in medicines, toxicants, perfumes, seasonings, pigments and the like. When it is desired that the separated aglycone is in the form of a certain glycoside for a particular use, the aglycone can be converted into a desired glycoside according to a conventional reaction such as condensation of an acetohalogenose with the aglycone by using silver carbonate, silver oxide, mercury acetate or the like, condensation of an acetylated sugar and phenol with heating in the presence of p-toluenesulfonic acid or zinc chloride, or the like.

Now, one embodiment of the present invention is illustrated by using FIG. 1.

FIG. 1 shows a flow sheet of a batchwise extraction according to the method of the present invention by using $CO_2$ as an extraction agent. In FIG. 1, $CO_2$ is fed to a compressor (2) from a $CO_2$ cylinder (1) to compress it to a prescribed pressure and then fed to a heat exchanger (3) to heat it to a prescribed extraction temperature to obtain $CO_2$ at subcritical or supercritical conditions. This $CO_2$ is introduced into an extractor (4). In the extractor (4), there has been charged a plant, its dried and pulverized material or a material which has been separately hydrolyzed to decomposed into an aglycone and a sugar moiety as a starting material. When a plant or its dried and pulverized material has been charged, it is firstly subjected to hydrolysis and then extraction with $CO_2$, or it is subjected to hydrolysis during extraction with $CO_2$. When the hydrolyzed material is charged, it is directly subjected to extraction with $CO_2$. After completion of extraction, the $CO_2$ phase which contains an objective extract is passed through a pressure reducing valve (5) to reduce the pressure and led to a separator (6) to separate the extract from $CO_2$.

$CO_2$ thus separated from the extract is cooled and liquefied in a condenser (7) and led to the compressor (2) to recycle it in the system. In the case that an entrainer such as water or a lower alcohol (e.g., ethanol) is used, the entrainer is charged in the extractor (4) by mixing it with the starting material, or the entrainer is fed to the heat exchanger (3) from an entrainer holding tank (8) through a pump (9). In this system, it is necessary to maintain a $CO_2$ pressure in the extractor at 50 to 500 kg/cm$^2$, preferably, 60 to 300 kg/cm$^2$, and a temperature at 25°to 100° C., preferably, 25°to 70° C. When the the temperature are too low, $CO_2$ is liquefied and energy is required in separation of the extract from the extraction agent. On the other hand, when they are too high, the equipment cost is increased and economical problems are raised. In addition, sometimes, adverse effects such as heat deterioration will appear. In the separator (6), a better result can be obtained when the extract is separated from the $CO_2$ phase under conditions of the pressure at 1 to 200 kg/cm$^2$ and the temperature at 30°to 100° C. It is possible to effect a stepwise extraction by introducing the extraction agent to the extractor (4) with increasing the pressure thereof stepwise. Further, it is possible to provide a plurality of extractors in parallel to effect semi-continuous operation by switching one extractor to another. Usually, the separation of the extract from the extraction agent can be carried out by reducing the pressure as described above, but the separation can be also carried out by changing the temperature because the solubility is decreased with increasing in the extraction temperature.

Generally, in the process shown in FIG. 1, the extract is separated from the extraction agent in the separator (6) with time, and the components in the extract separated from the separator are varied depending upon a fractionation manner employed. Therefore, the desired active component in the extract can be obtained by appropriately choosing the fractionation manner.

The following Examples further illustrate the present invention in detail but are not to be construed to limit the scope thereof.

EXAMPLE 1

50 ml Aliquots of a medium shown in Table 1 which contained 1% ammonium glycyrrhizinate were distributed in 500 ml conical flasks and sterilized at 120° C. for 10 minutes. A loopful of *Aeromonas hydrophila* IFO 13282 was inoculated to each flask and cultivated with shaking at 30° C. for 24 hours. This procedure was repeated to obtain 1 liter of the culture medium. The culture medium was extracted in the extraction system as shown in FIG. 1 by charging it in the extractor and extracting with $CO_2$ at 35° C. under the pressure of 240 kg/cm$^2$. The extract was separated at the normal temperature under atmospheric pressure to obtain an isolated material (6.4 g). The isolated material was analyzed by gas chromatography and it was found that glycyrrhetic acid (4.1 g) was contained in the isolated material.

TABLE 1

| Composition of medium | |
|---|---|
| Ingredients | Concentration (g/l) |
| Ammonium glycyrrhizinate | 10.0 |
| $(NH_4)_2SO_4$ | 3.0 |
| $KH_2PO_4$ | 5.0 |
| $MgSO_4.7H_2O$ | 0.5 |
| $MnCl_2.4H_2O$ | 0.005 |
| $FeSO_4.7H_2O$ | 0.005 |
| Polypeptone | 0.5 |
| | (pH 5.2) |

EXAMPLE 2

Conc. sulfuric acid (10 g) was added to 10% aqueous solution of glycyrrhizin and the mixture was subjected to hydrolysis under reflux for 12 hours. Then, pH was adjusted to 6 with 5% aqueous sodium hydroxide solution and the mixture was extracted in the extraction system as shown in FIG. 1 by charging it in the extractor, extracting with $CO_2$ at 37° C. under pressure of 250 kg/cm$^2$, separating the extract at the normal temperature under atmospheric pressure to obtain an isolated material (2.3 g).

The isolated material was analyzed by gas chromatography and it was found that glycyrrhetic acid (1.7 g.) was contained in the isolated material.

EXAMPLE 3

Pulverized apricot seed (800 g) was charged in the extractor as shown in FIG. 1 and extracted with $CO_2$ at 40° C. under the pressure of 200 kg/cm$^2$ to extract and remove a non drying oil in apricot seed. The pressure was reduced to atmospheric pressure at the normal temperature to separate the extract from the extraction agent to remove crude apricot kernel oil (315 g).

After removal of the non drying oil, water (300 g) was added to the extractor in which the pulverized apricot seed was charged to activate the enzyme, emulsin contained therein. While hydrolysis with emulsin proceeded, extraction was carried out with $CO_2$ at 40° C. under the pressure of 150 kg/cm$^2$. Separation of $CO_2$ was the normal temperature under atmospheric pressure. By carrying out extraction for 10 hours, the extract (3.3 g) was obtained. The extract was a liquid having unique aroma and the main component thereof is benzaldehyde.

The extract was able to use as a raw material for perfumes and medicines.

According to the present invention, an aglycone in a glycoside can be obtained in an industrially advantageous manner and, in comparison with a conventional manner, the following distinguished advantages can be attained.

(1) It has been considered heretofore that use of carbon dioxide at supercritical conditions in extraction of a glycoside is difficult. However, according to the present invention, an aglycone which is a substantial effective component of a glycoside can be readily extracted in an improved yield. Thus, the method of the present invention is an epoch-making process for extracting an aglycone.

(2) Deterioration of an aglycone can be completely prevented because extraction is carried out at a relatively low temperature under an inert atmosphere.

(3) Since carbon dioxide used as the extraction agent is rapidly evaporated during the separation step, problems due to remaining of a solvent can be avoided.

(4) The steps are quite simple and it is possible to effect selective separation and fractionation in a high yield.

In many cases, a specific component is concentrated in each fraction of the fractionated extract and it is suitable for a subsequent precise fractionation. Further, flavors and the like can be incorporated with each other in an appropriate proportion to obtain a desired aroma.

What is claimed is:

1. A method for extracting and separating an aglycone from a glycoside, said method comprises steps of:

subjecting a material containing the glycoside to hydrolysis to decompose the glycoside into a sugar moiety and an aglycone:

extracting the aglycone from the hydrolyzed material by using carbon dioxide at supercritical or subcritical conditions as an extraction agent; and separating the extracted aglycone from the extraction agent.

2. A method for extracting and separating an aglycone from a glycoside, said method comprising the steps of:

subjecting a material containing the glycoside to hydrolysis to decompose the glycoside into a sugar moiety and an aglycone;

extracting the aglycone from the hudrolyzed material by using carbon dioxide at subcritical conditions as an extraction agent; and separating the extracted aglycone from the extraction agent.

3. A method according to claim 1 or claim 2, wherein hydrolysis and extraction are carried out simultaneously.

4. A method according to claim 1, wherein carbon dioxide is at a pressure of 50 to 500 kg/cm$^2$ and a temperature of 25° to 100° C.

5. A method according to claim 1, wherein an entrainer is incorporated with carbon dioxide said entrainer being selected from the group consisting of water, lower alcohol or a combination of water and a lower alcohol.

6. A method according to claim 5, wherein the lower alcohol is ethanol.

7. A method according to claim 1 or claim 2, wherein separation is carried out at 30 to 100° C. under pressure of 1 to 200 kg/cm$^2$.

8. A method according to claim 1 or claim 2, wherein the extract is fractionated into components by effecting stepwise extraction or fractional separation.

9. A method according to claim 1 or claim 2, wherein an aglycone extracted in the extraction step is passed through a layer of a host compound which forms an inclusion complex to obtain the aglycone in the form of a stable inclusion complex.

10. A method according to claim 9, wherein the host compound is cyclodextrin.

* * * * *